(12) United States Patent
Gentala et al.

(10) Patent No.: US 8,838,396 B2
(45) Date of Patent: *Sep. 16, 2014

(54) REMOTE VEHICLE EMISSIONS SENSING SYSTEM AND METHOD FOR DIFFERENTIATING WATER FROM HYDROCARBONS

(71) Applicant: Envirotest Systems Holdings Corp., East Granby, CT (US)

(72) Inventors: Robert Allen Gentala, Tucson, AZ (US); Peter Miles McClintock, Tiburon, CA (US); Donald Hugh Stedman, Denver, CO (US)

(73) Assignee: Envirotest Systems Holdings Corp., East Granby, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/897,992

(22) Filed: May 20, 2013

(65) Prior Publication Data

US 2013/0253849 A1 Sep. 26, 2013

Related U.S. Application Data

(63) Continuation of application No. 12/643,208, filed on Dec. 21, 2009, now Pat. No. 8,447,528.

(51) Int. Cl.
*G01N 31/00* (2006.01)
*G01N 21/31* (2006.01)
*G01N 21/35* (2014.01)
*G01N 21/17* (2006.01)

(52) U.S. Cl.
CPC ........ *G01N 21/31* (2013.01); *G01N 2021/1793* (2013.01); *G01N 21/3504* (2013.01)
USPC ............... 702/24; 702/23; 702/100; 702/104; 702/179; 702/189

(58) Field of Classification Search
USPC .......... 702/23, 24, 100, 104, 179, 189; 701/1; 250/338.5; 73/23.31, 114.71
See application file for complete search history.

(56) References Cited

U.S. PATENT DOCUMENTS 3,364,351 A 1/1968 Palmer et al.
4,360,336 A 11/1982 Shepherd
(Continued)

FOREIGN PATENT DOCUMENTS

EP 0 681 179 A1 2/1995
JP 08-043288 2/1996
(Continued)

OTHER PUBLICATIONS

Stockwell, Paul, "Tunable Diode Laser Systems Break New Ground in Water Vapour Analysis", IMA Ltd., West Yorkshire, United Kingdom, [undated], pp. 1-8.

(Continued)

*Primary Examiner* — Elias Desta
(74) *Attorney, Agent, or Firm* — Pillsbury Winthrop Shaw Pittman LLP (57) ABSTRACT

Water droplets in exhaust gas that is, or was, analyzed by a remote emissions sensing system are detected. The detection may be made using measurements generally captured by the remote emissions sensing system during typical operation. As such, the detection may be applied "on site" as remote emissions sensing analysis is ongoing, or may be applied post hoc from data previously acquired by a remote emissions sensing system. The detection may be implemented without requiring additional sensors, more sophisticated sensors, and/or other additional or more sophisticated equipment being included in the remote emissions sensing system.

7 Claims, 6 Drawing Sheets

(56) References Cited

U.S. PATENT DOCUMENTS

| | | | |
|---|---|---|---|
| 4,953,390 A | 9/1990 | Krempl et al. |
| 5,210,702 A | 5/1993 | Bishop et al. |
| 5,319,199 A | 6/1994 | Stedman et al. |
| 5,332,901 A | 7/1994 | Eckles et al. |
| 5,343,043 A | 8/1994 | Johnson |
| 5,371,367 A | 12/1994 | DiDomenico et al. |
| 5,401,967 A | 3/1995 | Stedman et al. |
| 5,418,366 A | 5/1995 | Rubin et al. |
| 5,457,320 A | 10/1995 | Eckles et al. |
| 5,489,777 A | 2/1996 | Stedman et al. |
| 5,498,872 A | 3/1996 | Stedman et al. |
| 5,591,975 A | 1/1997 | Jack et al. |
| 5,621,166 A | 4/1997 | Butler |
| 5,644,133 A | 7/1997 | Didomenico et al. |
| 5,719,396 A | 2/1998 | Jack et al. |
| 5,726,450 A | 3/1998 | Peterson et al. |
| 5,831,267 A | 11/1998 | Jack et al. |
| 6,307,201 B1 | 10/2001 | Didomenico et al. |
| 6,560,545 B2 | 5/2003 | Stedman et al. |
| 6,701,256 B2 | 3/2004 | Stedman et al. |
| 6,723,989 B1 | 4/2004 | Didomenico et al. |
| 6,789,021 B2 * | 9/2004 | Rendahl et al. ............... 702/22 |
| 6,983,639 B1 | 1/2006 | DiDomenico et al. |
| 7,016,789 B2 | 3/2006 | Stedman et al. |
| 7,049,595 B2 | 5/2006 | Kansakoski et al. |
| 7,141,793 B2 | 11/2006 | Johnson et al. |
| 7,164,132 B2 * | 1/2007 | Didomenico et al. ..... 250/338.5 |
| 7,359,804 B2 | 4/2008 | Williams et al. |
| 7,400,398 B2 | 7/2008 | Stedman |
| RE40,767 E | 6/2009 | Peterson et al. |
| 7,930,931 B2 | 4/2011 | Stedman |
| 8,266,952 B2 | 9/2012 | Stedman |
| 8,447,528 B2 * | 5/2013 | Gentala et al. ................ 702/24 |
| 2002/0052698 A1 | 5/2002 | Didomenico et al. |
| 2003/0089854 A1 | 5/2003 | Shifflett et al. |
| 2003/0120434 A1 | 6/2003 | DiDomenico et al. |
| 2004/0155191 A1 | 8/2004 | Stedman et al. |
| 2005/0197794 A1 | 9/2005 | Full |
| 2009/0272181 A1 | 11/2009 | Stedman |
| 2011/0153223 A1 | 6/2011 | Gentala et al. |
| 2011/0162435 A1 | 7/2011 | Stedman |
| 2011/0265552 A1 | 11/2011 | Stedman |
| 2012/0130584 A1 | 5/2012 | Stedman |

FOREIGN PATENT DOCUMENTS

| | | |
|---|---|---|
| WO | WO 92/12411 | 7/1992 |
| WO | WO 98/37405 | 8/1998 |
| WO | WO 00/34755 | 6/2000 |
| WO | WO 02/082059 | 10/2002 |

OTHER PUBLICATIONS

Guenther, Paul L., et al., "A Hydrocarbon Detector for the Remote Sensing of Vehicle Exhaust Emissions", *Review of Scientific Instruments*, vol. 66, No. 4, Apr. 1995, pp. 3024-3029.

Williams, Mitchell Jared, "Advances in On-Road Remote Sensing [Microform]: Feat 5000 the Next Generation", Thesis, University of Denver, MAS 2003 No. 27, Aug. 2003, 147 pages.

* cited by examiner

REMOTE VEHICLE EMISSIONS SENSING SYSTEM AND METHOD FOR DIFFERENTIATING WATER FROM HYDROCARBONS

CROSS-REFERENCE TO RELATED APPLICATIONS

This application is a continuation of U.S. patent application Ser. No. 12/643,208, filed Dec. 21, 2009 (which issued as U.S. Pat. No. 8,447,528 on May 21, 2013), which is hereby incorporated by reference herein in its entirety.

FIELD OF THE INVENTION

The invention relates generally to the remote measurement of vehicle emissions, and more particularly to a system and method for the detection of water droplets in remotely monitored vehicle emissions.

BACKGROUND OF THE INVENTION

Systems and methods for remotely monitoring the exhaust gas composition of motor vehicles are known. For example, a Remote Sensing System (RSS) positioned at a predetermined location along a roadway measures tailpipe emissions as vehicles pass through infrared (IR) and ultraviolet (UV) beams cast across the roadway. IR/UV light is typically reflected back across the roadway (e.g., via a transfer mirror module) to a series of detectors that monitor light intensity at characteristic wavelengths. By measuring the absorption of IR/UV light by the various pollutants in the air, the RSS is able to calculate pollutant concentrations in the exhaust plumes of passing vehicles.

More particularly, RSS exhaust emissions measurements comprise a series of periodic readings spanning a predetermined time period (e.g., approximately one-half second after the passing of a vehicle). Each reading gives the quantity of each gas of interest (e.g., in an exhaust plume) in the beam path. Because the amount of dilution of an exhaust plume at each instant is not known, the individual readings for each gas are ratioed, for example, to a corresponding carbon dioxide ($CO_2$) reading. These ratios of gas amounts remain constant throughout an exhaust plume, and are independent of dilution. The ratios themselves may be useful. For example, the ratios may be directly converted to mass of pollutant per mass of fuel, or can be used in conjunction with the combustion equation to convert the ratios into the gas concentrations which would be measured by a tailpipe probe when corrected for excess air and water. A combustion equation that assumes a particular fuel is used to convert the ratios into gas concentrations.

Remote emissions measurements rely on the ability of each gas of interest to absorb light of only certain wavelengths. A channel (for each gas of interest) compares the amount of light traversing the beam path in its particular frequency before the vehicle with the amount of light after the vehicle, and calculates the amount of gas from the absorbed light. To correct for fluctuations in the light source or light that may be blocked by particles, a reference channel is also used at a frequency where there is no gaseous absorption.

Over time, steady advances in the sophistication and robustness of remote sensing technology, together with the analysis of acquired vehicle emissions data, have resulted in a number of important findings. As an example, it has been determined that the presence of water droplets in vehicle exhaust emission plumes may cause erroneously high hydrocarbon (HC) readings. This may be especially problematic when attempting to measure evaporative emissions (e.g., vapors that vent into the air from hot engines and fuel systems) by noting high HC readings that are uncorrelated with accompanying $CO_2$ readings.

One prior approach for recognizing and rejecting erroneously high HC readings in remote emissions measurements includes the use of an additional IR channel that is twice as sensitive to water droplets as it is to gaseous HC. See WILLIAMS, Mitchell Jared, "*Advances in On-Road Remote Sensing: Feat 5000 The Next Generation*", Thesis, University of Denver, MAS 2003 No. 27, August 2003, which is hereby incorporated herein by reference in its entirety. Detections of elevated HC in the HC channel accompanied by readings that are twice as elevated in the additional IR channel are flagged as water droplet "steam" plumes. Use of this hardware-based approach, however, may result in both an increased time and expense associated with hardware configuration and/or calibration.

These and other drawbacks exist.

SUMMARY OF THE INVENTION

The invention addressing these and other drawbacks relates to a system and method for the detection of water droplets in remotely monitored vehicle emissions, including both exhaust emissions and evaporative emissions. The detection may be made using emissions data acquired by an RSS during typical operation. Accordingly, the detection may be made in real-time as data is acquired, or during post-processing of a previously-acquired emissions data set. Further, the system and method of the invention enable the detection of water droplets in remotely monitored vehicle emissions data without modifying an RSS to include additional sensors (or components) and/or more sophisticated sensors (or components).

According to an aspect of the invention, and as described in greater detail herein, an RSS system may comprise an electromagnetic radiation source, a detector, one or more processors, and/or other components. The source and detector may be configured such that an optical path between the source and the detector traverses a roadway along which a vehicle emitting exhaust gas travels. The source may emit electromagnetic radiation at wavelengths that are absorbed by a plurality of molecular species present in vehicle exhaust emitted by the vehicle. The molecular species may include, for example, hydrocarbons (HC), carbon monoxide (CO), carbon dioxide ($CO_2$), nitrogen oxides ($NO_x$) such as NO and $NO_2$, and/or other molecular species.

As such, the wavelengths at which electromagnetic radiation is emitted by the source and absorbed by molecular species may include a first absorption wavelength, a second wavelength, a third absorption wavelength, and/or additional absorption wavelengths. The first absorption wavelength may be a wavelength at which CO absorbs electromagnetic radiation, the second absorption wavelength may be a wavelength at which $CO_2$ absorbs electromagnetic radiation, and the third absorption wavelength may be a wavelength at which HC absorbs electromagnetic radiation.

For instance, CO may absorb electromagnetic radiation at or near 4.6 microns (e.g., the first absorption wavelength), HC may absorb electromagnetic radiation at or near 3.6 microns (e.g., the second absorption wavelength), and $CO_2$ may absorb electromagnetic radiation at or near 4.3 microns (e.g., the third absorption wavelength). These are provided merely for illustrative purposes. In some implementations, other particular molecular species may be used in accordance with this disclosure for the purposes of detecting the presence of water.

The electromagnetic radiation emitted by the source may further include electromagnetic radiation at one or more reference wavelengths. The one or more reference wavelengths may include wavelength(s) at which electromagnetic radiation is not substantially absorbed by any of the constituents commonly found in vehicle exhaust. For example, the reference wavelength may be at or near 3.9 microns.

According to an aspect of the invention, the one or more processors may be configured to provide information processing capabilities in the system. The one or more processors may be provided along with the source and the detector for analysis at a testing site. In some implementations, the one or more processors may include a first set of one or more processors physically present at the testing site, and a second set of one or more processors that process data acquired and/or processed at the testing site remotely in time and/or space from the acquisition of data at the testing site. Information may be transferred between the first set of processors to the second set of processors by a communication link, via removable electronic storage, and/or by other communication mechanisms.

The one or more processors may be configured to execute one or more computer program modules. The one or more computer program modules may include one or more of a quantity module, a ratio module, a trigger module, a residual module, a water analysis module, and/or other modules. The one or more processors may be configured to execute the modules by software, hardware, firmware, some combination of software, hardware, and/or firmware, and/or other mechanisms for configuring processing capabilities on the one or more processors.

In one implementation, the quantity module may be configured to determine preliminary quantities of one or more molecular species in the optical path. The quantity module may make this determination based on output signals generated by the detector indicating the intensity of electromagnetic radiation received at the detector in one or more absorption wavelengths. The intensities of the electromagnetic radiation received in the one or more absorption wavelengths may indicate amount of electromagnetic radiation in the one or more absorption wavelengths that have been absorbed and/or blocked along the optical path.

During operation, the intensities of electromagnetic radiation emitted by the source may vary. Such variation may be the result of ordinary operation, and/or may be enhanced by environmental and/or system factors. To account for these variations, the detector may generate one or more output signals indicating the received intensity of one or more reference wavelengths. Since electromagnetic radiation at the one or more reference wavelengths may not be significantly absorbed by exhaust gas, the quantity module may implement these output signals of the detector to correct for variation in the intensity of electromagnetic radiation emitted by the source.

In one implementation, the ratio module may be configured to determine ratios of the molecular species for which quantities are determined by the quantity module. The dilution of exhaust gas present in the optical path may not be known at a given point in time. As such, to determine the concentrations of molecular species, the ratio module determines ratios of molecular species because such ratios may be independent of dilution. For example, the ratio module may determine a ratio of CO to $CO_2$, and/or a ratio of HC to $CO_2$. The ratios determined by the ratio module may be converted to concentrations of the molecular species from a combustion equation that assumes a particular fuel.

Generally, vehicle exhaust includes relatively large quantities of water. When the water is in a gaseous state, the water may not substantially interfere with measurements of exhaust gas composition by the RSS. However, under certain ambient conditions, such as low temperatures and/or high humidity, for example, gaseous water present in exhaust may undergo a phase change and form minute liquid droplets having the appearance of white smoke, sometimes incorrectly referred to as "steam" or a "steam plume". These droplets may effectively block electromagnetic radiation at various wavelengths from ultra-violet spectrum, through the visible spectrum, and into the near infra-red spectrum. The wavelengths at which the liquid water blocks electromagnetic radiation may include wavelengths at which electromagnetic radiation is absorbed by one or more gaseous species in exhaust gas.

For example, in the spectrum from about 3 microns to about 5 microns, water droplets present in the optical path may block electromagnetic radiation. This portion of the spectrum may include the first absorption wavelength (e.g., corresponding to CO), the second absorption wavelength (e.g., corresponding to HC), a third absorption wavelength (e.g., corresponding to $CO_2$), and/or a reference wavelength as described above. In this portion of the spectrum, the ability of water droplets to block electromagnetic radiation may fall as wavelength increases. This drop in blockage of electromagnetic radiation by water droplets may be substantial for increasing wavelengths. As such, water droplets in the optical path may tend to have a very different impact on the electromagnetic radiation in the optical path at the first absorption wavelength, the second absorption wavelength, the third absorption wavelength, and/or the reference wavelength. This may negatively impact the accuracy of the quantity module and/or the ratio module.

In one implementation, the trigger module may be configured to trigger analysis to determine if water droplets are present in the optical path at a given point in time. This may include analyzing determinations of absorption and/or quantity of one or more molecular species for apparently anomalous readings. By way of non-limiting example, the amount of blockage caused by water droplets in the optical path may be much larger at the second absorption wavelength than in the reference wavelength. As was discussed above, the quantity module may implement the reference wavelength in correcting absorption at the second absorption wavelength to account for intensity variations at the source. This may result in determinations of apparent absorption at the second absorption wavelength (and/or of quantity of HC) that are higher than the actual amount of absorption (and/or quantity of HC).

In some implementations, the trigger module may monitor determinations of absorption at the second absorption wavelength and/or determinations of quantity of HC. The trigger module may trigger analysis to determine if water is present in the optical path if absorption at the second absorption wavelength and/or the quantity of HC are elevated. For example, further analysis may be triggered by the trigger module if absorption at the second absorption wavelength and/or the quantity of HC breach a predetermined threshold.

Because of the fall off in blockage by water droplets at ascending wavelengths, the blockage by water droplets will tend to impact determinations of absorption for absorption wavelengths other than the second absorption wavelength differently than determinations of absorption for the second absorption wavelength. This may enable the residual module and the water analysis module to detect the presence of water droplets in the optical path from a comparative analysis based on the determined absorptions at the various absorption wavelengths.

The impact of water droplets on the determination of absorption for absorption wavelengths that are larger than the second wavelength may be relatively small with respect to absorption by exhaust gas along the optical path at the larger absorption wavelengths. As such, before the impact of water droplets on the determinations of absorption for absorption wavelengths other than the second absorption wavelength can be used to detect the presence of the water droplets, the impact of the water droplets must be separated from the absorption by the exhaust gas.

In one implementation, the residual module may be configured to separate the actual absorption by exhaust gas from residual impact on electromagnetic radiation intensity caused by water droplet blockage at one or more absorption wavelengths. For example, to quantify the residual impact of water droplet blockage at the first absorption wavelength, the quantity of CO may be determined as a function of the measured quantity of another molecular species, such as $CO_2$. This determination may be made, for instance, by a regression line that correlates values of the quantity of CO determined by the quantity module with values of the quantity of $CO_2$ determined by the quantity module from contemporaneous measurements.

Once the quantity of CO as a function of $CO_2$ is determined, the residual impact which may be caused by water droplet blockage at the first absorption wavelength (separate from absorption by the first molecular species) may be determined according to the following relationship:

$$CO_{residual} = CO_{measured} - (a + m*CO_{2\ measured}) \quad (1)$$

where $CO_{residual}$ represents the residual impact of water droplet blockage at the first absorption wavelength on the determination of the quantity of CO;

$CO_{measured}$ represents the quantity of CO determined by the quantity module;

$CO_{2\ measured}$ represents the quantity of $CO_2$ determined by the quantity module; and $(a + m*CO_{2\ measured})$ represents an equation by which the quantity of CO can be determined as a function of $CO_{2\ measured}$.

Water droplets formed from exhaust gas will typically only be present in the optical path for a short period of time. As such, the correlation of $CO_{measured}$ with $CO_{2\ measured}$ to determine $CO(CO_{2\ measured})$, which uses measurements of $CO_{measured}$ and $CO_{2\ measured}$ over a far greater period of time than will be impacted by the water droplets, may also tend to reflect the relationship between $CO_{measured}$ and $CO_{2\ measured}$ when water droplets are not present in the optical path. For the purpose of calculation of $CO_{residual}$, if a negative correlation slope is obtained (m<0), then the negative m may be replaced with 0 in equation (1).

In one implementation, the water analysis module may be configured to analyze the residual impact of water droplet blockage at the first absorption wavelength on the determination of the quantity of CO and the quantity of HC made by the quantity module to determine if water droplet blockage is/was present in the optical path. For instance, the residual impact of water droplet blockage at the first absorption wavelength on the determination of the quantity of CO may be compared with the quantity of HC to determine if the values of both of these variables indicate the presence of water droplet blockage in the optical path.

By way of non-limiting example, the impact of water droplet blockage on determinations of HC may be inversely proportional to the impact of water droplet blockage on determinations of $CO_{residual}$. In the case of HC and CO, the proportionality factor may be on the order of $-10^{-4}$.

It will appreciated that the description of various implementations herein with respect to the specific molecular species CO, HC, and $CO_2$ are not intended to be limiting. Other implementations in which different molecular species are associated with a different first absorption wavelength, second absorption wavelength, and/or third absorption wavelength fall within the scope of this disclosure.

These and other objects, features, and characteristics of the invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the invention. As used in the specification and in the claims, the singular form of "a", "an", and "the" include plural referents unless the context clearly dictates otherwise.

DETAILED DESCRIPTION OF THE INVENTION

Prior to describing an exemplary method for the detection of water droplets in remotely monitored vehicle emissions, including both exhaust emissions and evaporative emissions, a description of an exemplary RSS will first be provided. Various implementations of the invention may include some or all of the RSS components as described below.

Exemplary Remote Sensing System (RSS)

Figure 1:
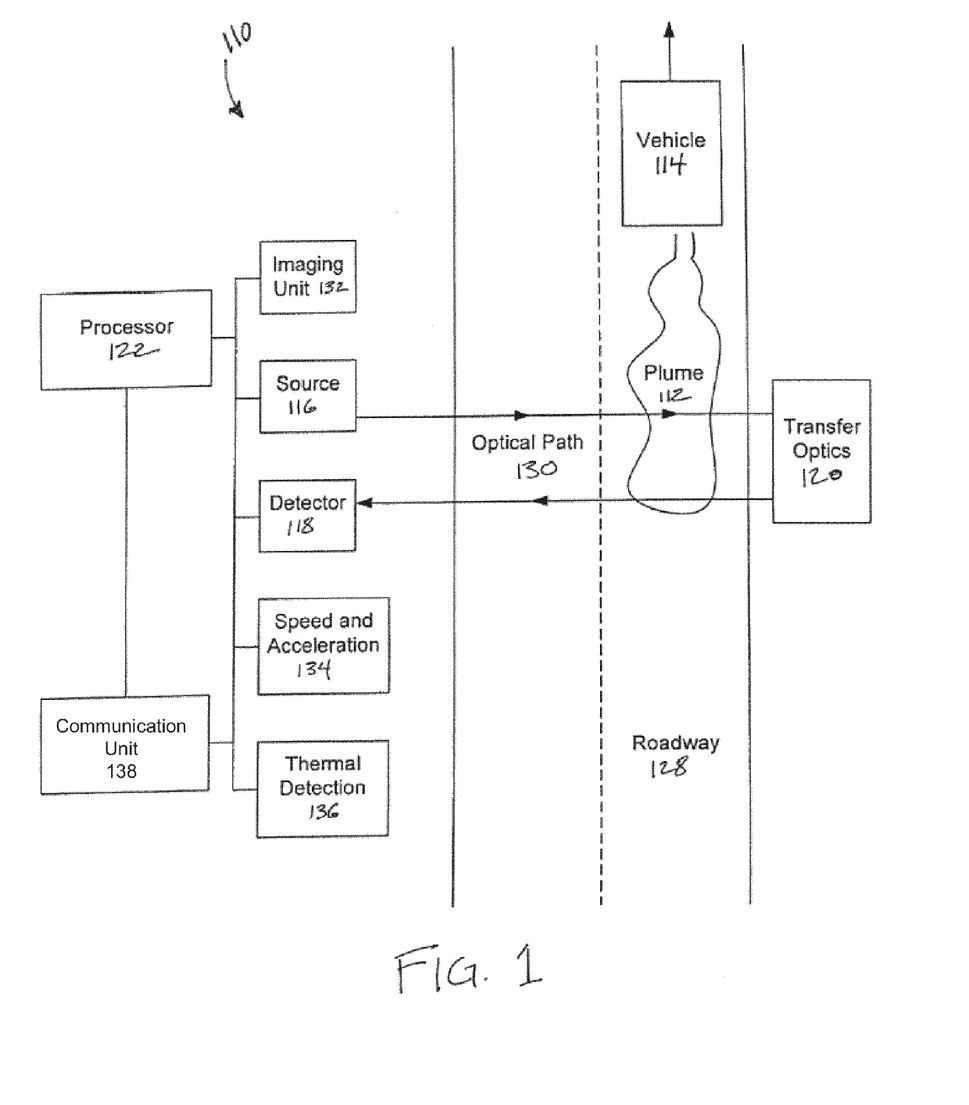
FIG. 1 is an exemplary illustration of an RSS system, according to an aspect of the invention.

FIG. 1 illustrates RSS 110 according to an implementation of the invention. RSS 110 measures emissions in an exhaust plume 112 (from a motor vehicle 114) in an optical (or measurement) path 130 on a roadway 128. Roadway 128 may comprise a single or multi-lane roadway, or any other roadway or driving surface suitable for the safe passage of vehicle 114 under various operating conditions. Alternatively, roadway 128 may comprise a test lane designated for vehicle emissions testing, wherein vehicle 114 may be tested under a variety of operating conditions. RSS 110 may comprise a source 116, a detector 118, a processor 122, and/or other components.

As previously recited, source 116 may comprise one or more sources of electromagnetic radiation (ER) and detector 118 is preferably chosen to permit detection of electromagnetic radiation emitted by source 116. Source 116 may be selected to provide electromagnetic radiation with spectral characteristics that facilitate the detection of one or more predetermined gases present in exhaust plume 112. For example, nitric oxide, ammonia, and sulfur dioxide may be measured using UV electromagnetic radiation. Nitrogen dioxide, for example, may be measured using electromagnetic radiation with a wavelength of 430 nm.

According to one implementation, RSS 110 may comprise transfer optics 120 configured to allow radiation from source 116 to be directed to detector 118 for analysis. Transfer optics 120 may comprise a mirror, flat mirror, lateral transfer mirror (LTM), vertical transfer mirror (VIM), retroreflector, or other device. In one implementation, transfer optics 120 may comprise a lateral transfer mirror to reflect radiation from source 116 along a path displaced laterally or vertically, depending on orientation, from the incident direction. Other configurations may be used.

Processor 122, as will be described further below, may employ software to accomplish desired analysis of collected and/or stored data, and to carry-out one or more of the processing operations described herein. Processor 122 may include one or more of a digital processor, an analog processor, a digital circuit designed to process information, an analog circuit designed to process information, a state machine, and/or other mechanisms for electronically processing information. Although processor 122 is shown in FIG. 1 as a single entity, this is for illustrative purposes only. In some implementations, processor 122 may include a plurality of processing units. These processing units may be physically located within the same device, or processor 122 may represent processing functionality of a plurality of devices operating in coordination. For example, in some implementations, processor 122 may include a first set of one or more processors physically present at a remote testing site at which source 116 and detector 118 are deployed, and a second set of one or more processors that process data acquired and/or processed at the testing site remotely in time and/or space from the acquisition of data at the testing site. Information may be transferred between the first set of processors to the second set of processors by a communication link, via removable electronic storage, and/or by other communication mechanisms.

With regard to an exhaust gas sample present in optical path 130, software may be used to calculate the relative amounts of various exhaust gas constituents, concentrations of various exhaust gas constituents (e.g., HC, $CO_2$, $NO_x$, CO, etc.), the decay rate (e.g., dissipation in time) of the exhaust constituents, and the opacity of the exhaust plume.

Processor 122 may further comprise software to accomplish other data analysis functions. For example, vehicle emission data may be checked for running losses. Running losses may typically include emission readings due to fuel system leaks on a vehicle (e.g., leaky fuel tank filler cap, fuel line, etc.), blow-by emissions (e.g., crank case emissions blowing by the piston rings), or other systematic losses.

Processor 122 may also include software to accomplish various vehicle owner notification functions. For example, the owner of a vehicle that has been recorded as being in compliance with certain predetermined emission levels may receive a notification (e.g., via regular mail, electronic mail, text message, facsimile, recorded telephone communication, or the like). Coordination with local authorities may be arranged to grant vehicle owners a waiver or pass of local emission certification procedures upon receiving such a notification. Likewise, vehicles that fail to meet predetermined emission levels may receive a notification requiring the owner to remedy the non-compliance. Other data processing functions are also possible. Processor 122 may also interface to, control, and/or collect and reduce data from an imaging unit 132, a speed and acceleration detection unit 134, and thermal detection unit 136.

In various implementations, RSS 110 may comprise an imaging unit 132 to capture and/or record an image of vehicle 114 passing by (or through) RSS 110 in a known manner. Imaging unit 132 may be positioned to record an image of vehicle 114 at any predetermined number of locations. Imaging unit 132 may comprise, for example, a film camera, video camera, or digital camera. Other imaging devices may also be used.

In one implementation, imaging unit 132 may record an image of the identification tag (e.g., license plate) of vehicle 114. Tag information may be processed by processor 122 to provide additional information about the vehicle. For example, Motor Vehicle Department databases may be accessed to retrieve owner information, make, model type, model year, or other information. In some implementations, this additional information may be incorporated into the emission sensing data analysis. For example, the make and model year of the vehicle may be used to determine input information for certain processing steps, including information such as whether the vehicle includes a carburetor or fuel injector, whether the car runs on diesel fuel or gasoline, etc.

According to an implementation of the invention, RSS 110 may include a speed and acceleration detection unit 134. Preferably, the speed and/or acceleration of vehicle 114 may be measured as it passes through RSS 110 using speed and acceleration detection unit 134 in a known manner.

In one implementation, speed and acceleration detection unit 134 may comprise an arrangement of laser beams or other light beams associated with timing circuitry. The laser or light beams may be arranged to traverse the path of vehicle 114 at various points. As vehicle 114 passes, it will cause interruptions in the laser or light beams. The times at which the beam interrupts occur may be used to calculate the vehicle's speed and/or acceleration. Other methods of determining vehicle speed and/or acceleration may also be used or incorporated into RSS 110.

Alternatively, the laser or light beams or radar beams may be arranged to intercept the path of vehicle 114 as it drives along roadway 128. For example, radar systems may be used to determine vehicle speed and acceleration. Alternatively, transducers, piezoelectric elements, or other "drive over" detectors may be placed at locations in the roadway to monitor vehicle passage. Preferably, speed and/or acceleration data may be input into processor 122 to help characterize vehicle operating conditions (e.g., accelerating or decelerating), or to determine which vehicle is to be associated with a particular sensor measurement. Other configurations and uses of speed and acceleration data are also possible.

Some implementations of the invention may incorporate a thermal detection unit 136. Preferably, thermal detection unit 136 may comprise a non-contact thermometer system. For example, an IR thermometer may be used to optically detect the temperature of remote objects. Other temperature detection systems may also be used. Thermal detection unit 136 may, for example, be used to detect the temperature of portions of the vehicle passing through RSS 110. Some implementations may use direct sensing of the area of interest. For example, an IR thermometer may be aimed at the underside of a passing vehicle to detect the temperature(s) of vehicle components (e.g., engine, catalytic converter, muffler, etc.). Indirect sensing may also be used. For example, an IR thermometer may be aimed at the roadway to measure the heat of the passing vehicle which is reflected from the roadway surface.

Thermal information that is detected by thermal detection unit 136 may be used to indicate that an engine has just recently been started (e.g., the engine is "cold" or has not reached normal operating temperature). Such a cold engine reading may be used, for example, to initiate an alternative data processing routine. Certain implementations of the invention may reduce the chance of a potentially misleading reading by also detecting the temperature of other portions of the vehicle. Other uses for collected thermal data are also possible. Thermal detection of the exhaust plume of a vehicle and/or ambient temperatures may also be used in connection with various aspects of the invention.

According to one implementation of the invention, an identification tag on vehicle 114 may be read to identify the vehicle and associate particular sensed vehicle emission information with the vehicle. An identification tag, defined as a license plate above, may also comprise a transponder located on or within vehicle 114 (e.g., hung from a rear view mirror, placed on the dashboard, etc.), or that is integral within the vehicle (e.g., part of a global positioning system ("GPS"), located within the engine of the vehicle, or placed or mounted elsewhere). The transponder may transmit information about vehicle 114, including make and model of vehicle 114, engine characteristics, fuel type, the owner of vehicle 114, or other information which may be pertinent. According to an implementation, a transponder may be used in connection with other functions. For instance, a transponder may also be used in connection with a toll pass, whereby a driver can electronically pay tolls via the transponder without stopping the vehicle.

An identification tag may also comprise a tag or decal that requires a reader. By way of example, an identification tag may comprise a decal with identifying marks (e.g., bar codes, infrared markings, etc.) containing information about vehicle 114. The decal may be located outside vehicle 114, such as on a front or rear bumper, on the under-side of vehicle 114, or any other location on vehicle 114 where the decal may be suitably read. A reader may observe the decal and thereby obtain information about vehicle 114. One implementation employs a bar code placed on the roof of vehicle 114, which can be read by a reader placed above vehicle 114.

A receiver may be used to obtain information from an identification tag. According to an implementation of the invention, an antenna may receive signals transmitted from an identification tag containing a transponder. Any type of conventional receiver may be used to receive signals. According to an implementation of the invention, one reader and/or receiver may be used in connection with multiple lanes. Based on the signal received or the decal read, a receiver or reader may determine in which lane a particular vehicle is located at a particular time.

According to an implementation of the invention, processor 122 may receive vehicle information. For example, processor 122 may receive information about vehicle 114 from a reader and/or receiver. Vehicle information and information obtained by sensing vehicle emissions may be stored. Processor 122 may correlate vehicle information received from an identification tag with the results from vehicle emissions sensing. Processor 122 may update a vehicle record to account for the results obtained by processing vehicle emission data, such as information regarding whether a vehicle has passed or failed predetermined emissions criteria.

According to an implementation of the invention, RSS 110 may further comprise a communication unit 138. Communication unit may communicate information such as, for example, measured vehicle emissions and identification tag information from RSS 110 to various other locations (e.g., Motor Vehicle Departments, a central data repository, servers, etc.) for storage, processing, viewing, or other use in a known manner. Communication unit may transmit and/or receive information via a wired connection, such as cable or telephone line, or a wireless connection, such as by a radio, cellular, or satellite transmitter, or via any other type of suitable wireless communication.

In some implementations, communication unit 138 may comprise appropriate hardware and/or software to enable processor 122 to be accessed remotely over a network (not illustrated) via a communications link (not illustrated). The network may include any one or more of, for instance, the Internet, an intranet, a PAN (Personal Area Network), a LAN (Local Area Network), a WAN (Wide Area Network), a SAN (Storage Area Network), or a MAN (Metropolitan Area Network). The communications link may include any one or more of, for instance, a telephone line, a Digital Subscriber Line (DSL) connection, a Digital Data Service (DDS) connection, an Ethernet connection, an Integrated Services Digital Network (ISDN) line, an analog modem connection, a cable modem connection, or a wireless connection. In this regard, a user (e.g., an emissions test administrator or other individual) at a remote computer terminal can administer emissions tests, and/or analyze or process data. Thus, RSS 110 may, in various implementations, comprise either manned or unmanned systems.

As recited above, alternative RSS 110 configurations may exist incorporating some or all of the aforementioned system components. As an example, in certain implementations (not illustrated), source 116 and detector 118 may be placed on opposite sides of roadway 128. Various components of speed and acceleration detection unit 134 and thermal detection unit 136 may also be positioned on opposite sides of roadway 128.

In another implementation (not illustrated), RSS 110 may comprise a compact, unmanned system that may be used for unattended monitoring of vehicle emissions data (also referred to as a "bunkered" unit). In such an implementation, source 116, detector 118, imaging unit 132, processor 122, communication unit 138, and various components of speed and acceleration detection unit 134 and thermal detection unit 136 may be housed together on a first side of roadway 128, while transfer optics 120 and various other components of speed and acceleration detection unit 134 and thermal detection unit 136 may be housed together on the opposite side of roadway 128. Other configurations are possible. Accordingly, RSS 110 (as illustrated in FIG. 1) should not be viewed as limiting.

Detection of Water Droplets in Vehicle Emissions

Figure 2:
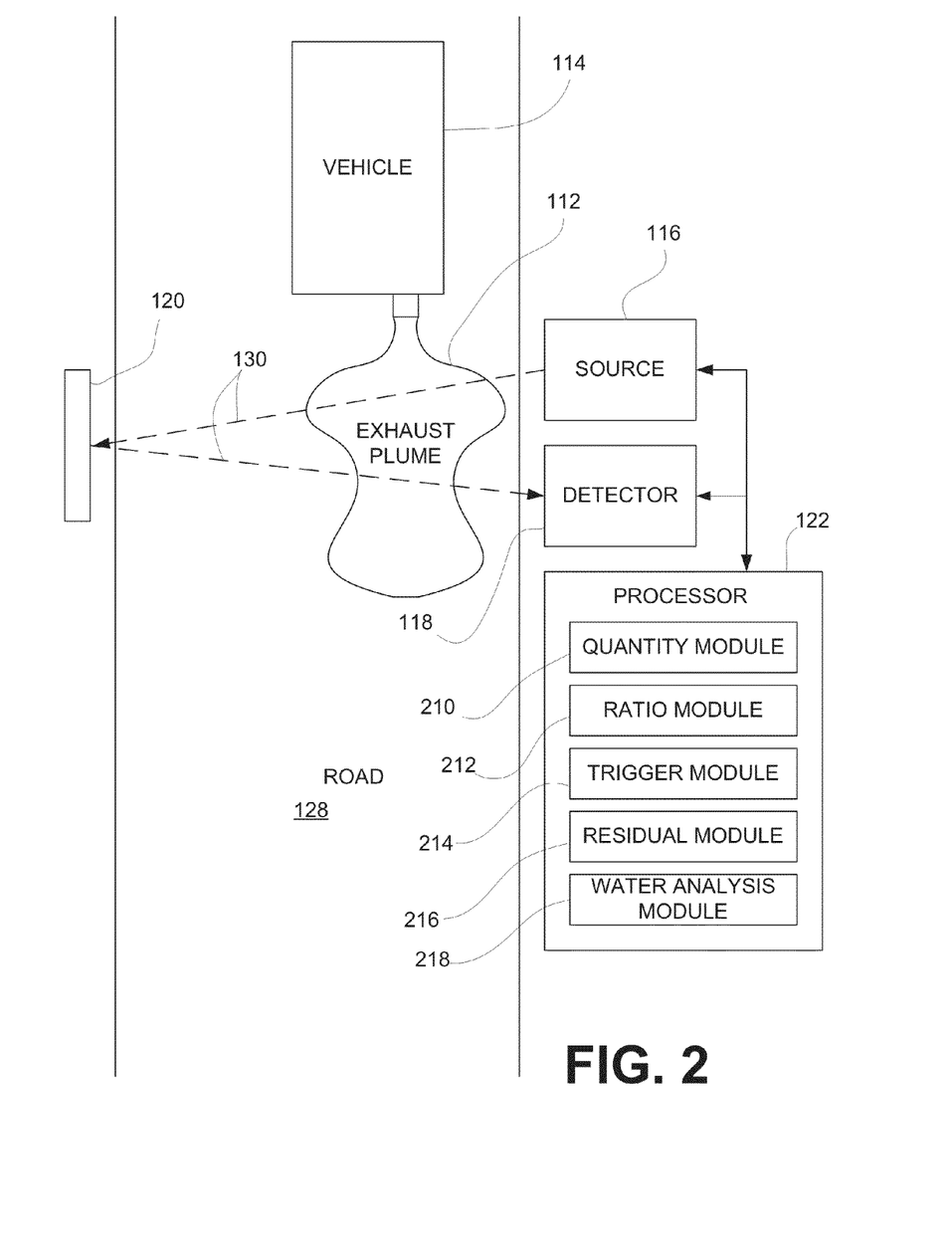
FIG. 2 is an exemplary illustration of an RSS system, according to an aspect of the invention.

FIG. 2 is an exemplary illustration of RSS 110, further depicting various computer program modules (described in detail below) that may be executed on processor 122.

Although not all of the components of RSS 110 that were depicted in FIG. 1 have been reproduced in FIG. 2, it should be understood that any one or more of the components described with reference to FIG. 1 may be implemented.

As shown in FIG. 2, source 116 may emit electromagnetic radiation at wavelengths that are absorbed by a plurality of molecular species present in vehicle exhaust including, for example, hydrocarbons (HC), carbon monoxide (CO), carbon dioxide ($CO_2$), nitrogen oxides ($NO_x$) such as NO and $NO_2$, and/or other molecular species. As such, the wavelengths at which electromagnetic radiation is emitted by source 116 and absorbed by molecular species may include a first absorption wavelength, a second wavelength, a third absorption wavelength, and/or additional absorption wavelengths. The first absorption wavelength may be a wavelength at which a first molecular species absorbs electromagnetic radiation, the second absorption wavelength may be a wavelength at which a second molecular species absorbs electromagnetic radiation, and the third absorption wavelength may be a wavelength at which a third molecular species absorbs electromagnetic radiation.

For instance, the first molecular species may be CO, which may be absorb electromagnetic radiation at or near 4.6 microns (e.g., the first absorption wavelength). The second molecular species may be HC, which may absorb electromagnetic radiation at or near 3.6 microns (e.g., the second absorption wavelength). The third molecular species may be $CO_2$, which may absorb electromagnetic radiation at or near 4.3 microns (e.g., the third absorption wavelength). These are provided merely for illustrative purposes. In some implementations, other particular molecular species may be used in accordance with this disclosure for the purposes of detecting the presence of water.

The electromagnetic radiation emitted by source 116 may further include electromagnetic radiation at one or more reference wavelengths. The one or more reference wavelengths may include wavelength(s) at which electromagnetic radiation is not substantially absorbed by any of the constituents commonly found in vehicle exhaust. For example, the reference wavelength may be at or near 3.9 microns.

It will be appreciated that the discussion of individual absorption and/or reference wavelengths herein may not be restricted to precise, individual wavelengths. As used herein, a given absorption or reference wavelength may include a band of wavelengths around a central wavelength.

As shown in FIG. 2, processor 122 may be configured to execute one or more computer program modules. The one or more computer program modules may include one or more of a quantity module 210, a ratio module 212, a trigger module 214, a residual module 216, a water analysis module 218, and/or other modules. Processor 122 may be configured to execute modules 210, 212, 214, 216, and/or 218 by software, hardware, firmware, some combination of software, hardware, and/or firmware, and/or other mechanisms for configuring processing capabilities on processor 122.

It should be appreciated that although modules 210, 212, 214, 216, and 218 are illustrated in FIG. 2 as being co-located within a single processing unit, in implementations in which processor 122 includes multiple processing units, one or more of modules 210, 212, 214, 216, and/or 218 may be located remotely from the other modules. The description of the functionality provided by the different modules 210, 212, 214, 216, and/or 218 described below is for illustrative purposes, and is not intended to be limiting, as any of modules 210, 212, 214, 216, and/or 218 may provide more or less functionality than is described. For example, one or more of modules 210, 212, 214, 216, and/or 218 may be eliminated, and some or all of its functionality may be provided by other ones of modules 210, 212, 214, 216, and/or 218. As another example, processor 122 may be configured to execute one or more additional modules that may perform some or all of the functionality attributed below to one of modules 210, 212, 214, 216, and/or 218.

According to one implementation of the invention, quantity module 210 may be configured to obtain preliminary quantities of one or more molecular species in optical path 130. The quantity module 210 may obtain the preliminary quantities from one or more external information resources (not shown) storing previously determined preliminary quantities of the one or more molecular species. The quantity module 210 may obtain the preliminary quantities by determining the quantities based on output signals generated by detector 118 indicating the intensity of electromagnetic radiation received at detector 118 in one or more absorption wavelengths. The intensities of the electromagnetic radiation received in the one or more absorption wavelengths may indicate an amount of electromagnetic radiation in the one or more absorption wavelengths that have been absorbed and/or blocked along optical path 130. The quantity module 210 may determine the absorption of electromagnetic radiation at the one or more absorption wavelengths based on the intensity of the electromagnetic radiation emitted by source 116 at the one or more absorption wavelengths and the output signals of detector 118. From the absorption at the one or more absorption wavelengths along optical path 130, quantity module 210 may determine the preliminary quantities of the corresponding one or more molecular species. For example, quantity module 210 may determine a preliminary quantity of CO, HC, and/or $CO_2$.

During operation, the intensities at which electromagnetic radiation at the one or more absorption wavelengths are emitted by source 116 may vary. Such variation may be the result of ordinary operation, and/or may be enhanced by environmental and/or system factors. To account for these variations in determining the absorptions of electromagnetic radiation at the one or more absorption wavelengths along optical path 130, detector 118 may generate one or more output signals indicating the received intensity of one or more reference wavelengths. Since electromagnetic radiation at the one or more reference wavelengths may not be significantly absorbed by exhaust gas, quantity module 210 may implement these output signals of detector 118 to correct for variation in the intensity of electromagnetic radiation emitted by source 116.

The ratio module 212 may be configured to determine ratios of the molecular species for which quantities are determined by quantity module 210. The dilution of exhaust gas present in optical path 130 may not be known at a given point in time. As such, to determine the concentrations of molecular species, ratio module 212 determines ratios of molecular species because such ratios may be independent of dilution. For example, ratio module 212 may determine a ratio of CO to $CO_2$, and/or a ratio of HC to $CO_2$. The ratios determined by ratio module 212 may be converted to concentrations of the molecular species from a combustion equation that assumes a particular fuel.

As previously noted, vehicle exhaust includes relatively large quantities of water. When the water is in a gaseous state, the water may not substantially interfere with measurements of exhaust gas composition by RSS 110. However, under certain ambient conditions, such as low temperatures and/or high humidity, for example, gaseous water present in exhaust may undergo a phase change and form minute liquid droplets having the appearance of white smoke, sometimes incorrectly referred to as "steam" or a "steam plume". These droplets may effectively block electromagnetic radiation at various wavelengths from ultra-violet spectrum, through the visible spectrum, and into the near infra-red spectrum. The wavelengths at which the liquid water blocks electromagnetic radiation may include wavelengths at which electromagnetic radiation is absorbed by one or more gaseous species in exhaust gas.

For example, in the spectrum from about 3 microns to about 5 microns, water droplets present in optical path 130 may block electromagnetic radiation. This portion of the spectrum may include the first absorption wavelength, the second absorption wavelength, a third absorption wavelength, and/or a reference wavelength as described above. In this portion of the spectrum, the ability of water droplets to block electromagnetic radiation may fall as wavelength increases. This drop in blockage of electromagnetic radiation by water droplets may be substantial for increasing wavelengths. As such, water droplets in optical path 130 may tend to have a very different impact on the electromagnetic radiation in optical path 130 at the first absorption wavelength, the second absorption wavelength, the third absorption wavelength, and/or the reference wavelength. This may negatively impact the accuracy of quantity module 210 and/or ratio module 212.

The trigger module 214 may be configured to trigger analysis to determine if water droplets are present in optical path 130 at a given point in time. This may include analyzing determinations of absorption and/or quantity of one or more molecular species for apparently anomalous readings. By way of non-limiting example, the amount of blockage caused by water droplets in optical path 130 may be much larger at the second absorption wavelength than in the reference wavelength. As was discussed above, quantity module 210 may implement the reference wavelength in determining absorption at the second absorption wavelength to account for intensity variations at source 116. This may result in determinations of absorption at the second absorption wavelength (and/or of HC) that are higher than the actual amount of absorption (and/or quantity of HC).

In some implementations, trigger module 214 may monitor determinations of absorption at the second absorption wavelength and/or determinations of quantity of HC. The trigger module 214 may trigger analysis to determine if water is present in optical path 130 if absorption at the second absorption wavelength and/or the quantity of HC are elevated. For example, further analysis may be triggered by trigger module 214 if absorption at the second absorption wavelength and/or the quantity of HC breach a predetermined threshold.

Figure 3:
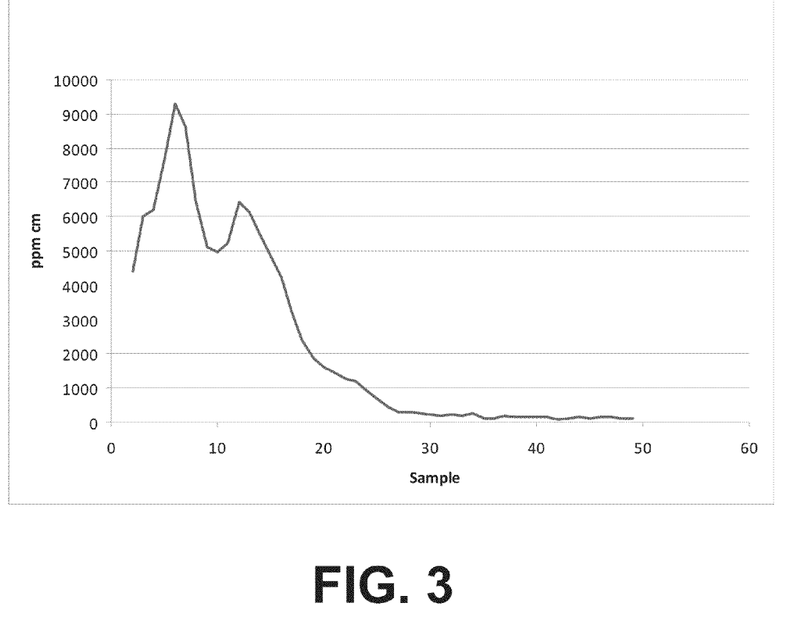
FIG. 3 illustrates an example of a plot of absorption (in an absorption wavelength) versus time, according to an aspect of the invention.

By way of illustration, FIG. 3 illustrates the manner in which droplets present in optical path 130 may cause temporary elevation for determinations of absorption of electromagnetic radiation at the second absorption wavelength. As can be seen in FIG. 3, the impact of water droplets present in optical path 130 on determinations of absorption of electromagnetic radiation at the second absorption wavelength, and/or determinations of the quantity of HC may be relatively strong. As such, analysis of determinations of absorption of electromagnetic radiation at the second absorption wavelength that identifies high levels of electromagnetic radiation attenuation along optical path 130 may be implemented to trigger further analysis of the absorption and/or quantity measurements.

Returning to FIG. 2, because of the fall off in blockage by water droplets at ascending wavelengths, the blockage by water droplets will tend to impact determinations of absorption for absorption wavelengths other than the second absorption wavelength differently than determinations of absorption for the second absorption wavelength. This may enable residual module 216 and water analysis module 218 to detect the presence of water droplets in optical path 130 from a comparative analysis based on the determined absorptions at the various absorption wavelengths.

The impact of water droplets on the determination of absorption for absorption wavelengths that are larger than the second wavelength may be relatively small with respect to absorption by exhaust gas along optical path 130. As such, before the impact of water droplets on the determinations of absorption for absorption wavelengths other than the second absorption wavelength can be used to detect the presence of the water droplets, the impact of the water droplets must be separated from the measured absorption by the exhaust gas.

The residual module 216 may be configured to separate the actual absorption by exhaust gas from residual impact on electromagnetic radiation intensity by water droplet blockage at one or more absorption wavelengths. For example, to quantify the residual impact of water droplet blockage at the first absorption wavelength, the quantity of CO may be determined as a function of the quantity of another molecular species, such as $CO_2$. This determination may be made, for instance, by a regression line that correlates values of the quantity of CO determined by quantity module 210 with values of the quantity of $CO_2$ determined by quantity module 210 from contemporaneous measurements.

Figure 4:
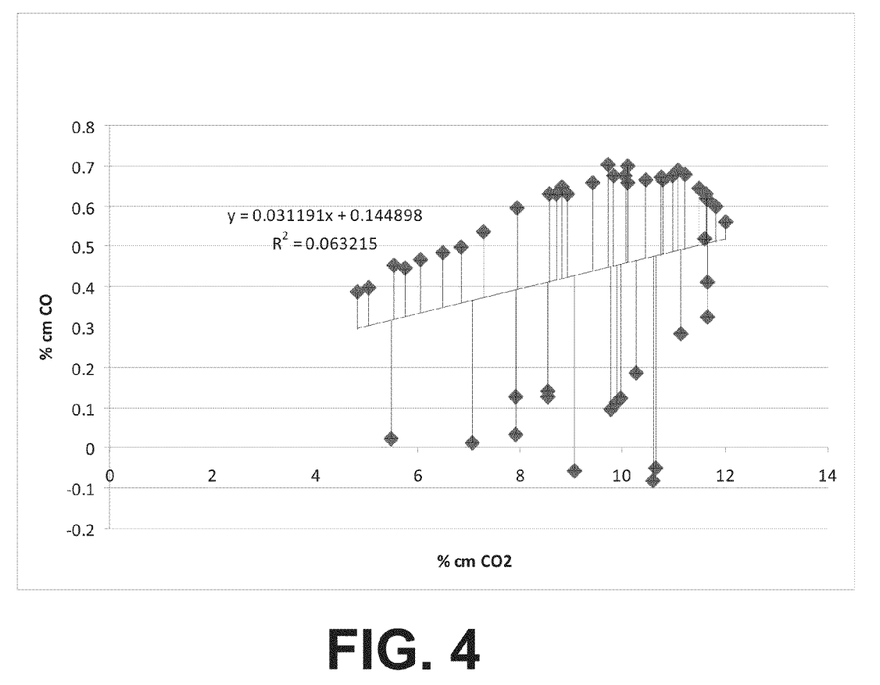
FIG. 4 is an illustrative depiction of a regression line that correlates determined quantities of a first molecular species with determined quantities of another molecular species, according to an aspect of the invention. The $CO_{residual}$ of each point is the distance up or down of each CO point from the line. In the illustration shown in FIG. 4, a~0.145, and m~0.0312.

By way of illustration, FIG. 4 illustrates a regression line that correlates determined quantities of CO with determined quantities of $CO_2$. FIG. 4 further illustrates residuals from the regression line corresponding to data points used to determine the regression line. This regression line may be associated with a function that describes the quantity of CO as a function of the quantity of $CO_2$. For example, the equation of the line (e.g., including the slope and intercept) may describe the quantity of CO as a function of the quantity of $CO_2$.

Returning to FIG. 2, once the quantity of CO as a function of $CO_2$ is determined, the residual impact of water droplet blockage at the first absorption wavelength (separate from absorption by the first molecular species) may be determined according to the following relationship:

$$CO_{residual} = CO_{measured} - (a + m \cdot CO_{2\,measured}) \qquad (2)$$

where $CO_{residual}$ represents the residual impact of water droplet blockage at the first absorption wavelength on the determination of the quantity of CO;

$CO_{measured}$ represents the quantity of CO determined by the quantity module;

$CO_{2\,measured}$ represents the quantity of $CO_2$ determined by the quantity module; and $(a + m \cdot CO_{2\,measured})$ represents a function that describes the quantity of CO as a function of $CO_{2\,measured}$.

Water droplets formed from exhaust gas will typically only be present in the optical path for a short period of time. As such, the correlation of $CO_{measured}$ with $CO_{2\,measured}$ to determine $(a + m \cdot CO_{2\,measured})$, which uses measurements of $CO_{measured}$ and $CO_{2\,measured}$ over a far greater period of time than will be impacted by the water droplets, may tend to reflect the relationship between $CO_{measured}$ and $CO_{2\,measured}$ when water droplets are not present in the optical path. For the purpose of calculation of $CO_{residual}$, if a negative correlation slope is obtained (m<0), then the negative m may be replaced with a 0 in equation (1).

The water analysis module 218 may be configured to analyze the residual impact of water droplet blockage at the first absorption wavelength on the determination of the quantity of CO and the quantity of HC made by quantity module 210 to determine if water droplet blockage is/was present in optical path 130. For instance, the residual impact of water droplet blockage at the first absorption wavelength on the determination of the quantity of CO may be compared with the quantity of HC to determine if the values of both of these variables indicate the presence of water droplet blockage in optical path 130.

Figure 5:
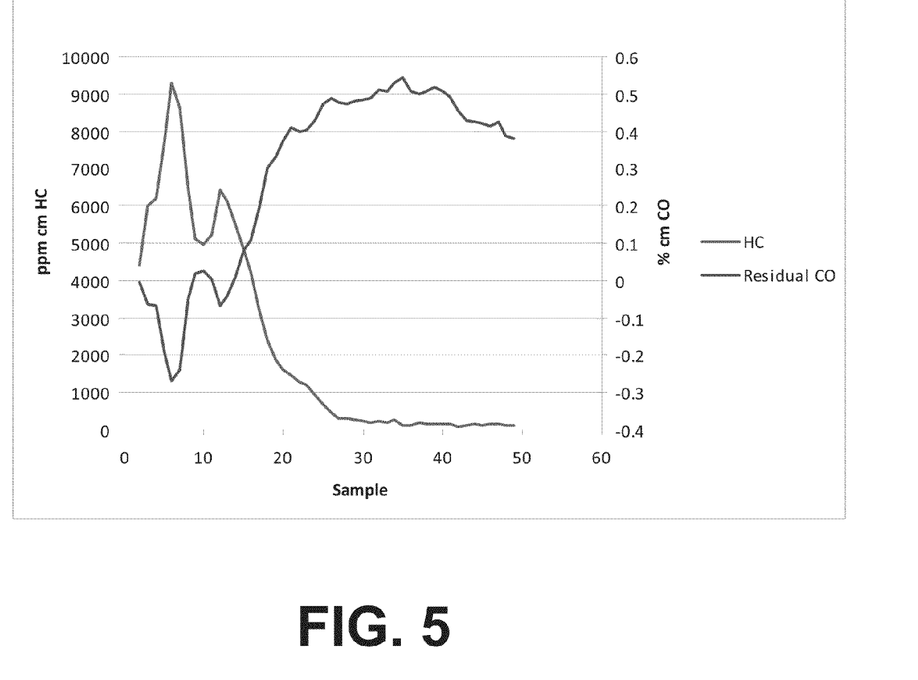
FIG. 5 illustrates plots of the residual impact of water droplet blockage at a first absorption wavelength on the determination of the quantity of a first molecular species and of the determined quantity of another molecular species versus time, according to an aspect of the invention. A strong anti-correlation between HC and $CO_{residual}$ can be seen, and may illustrate that he observed apparently large HC is caused by water droplets (e.g., a steam plume).

By way of non-limiting example, the impact of water droplet blockage on determinations of HC may be inversely proportional to the impact of water droplet blockage on determinations of CO. In the case of HC and CO, the proportionality factor may be on the order of $-10^{-4}$. By way of illustration, FIG. 5 shows a plot depicting how the quantity of HC may be correlated with the residual impact of water droplet blockage at the first absorption wavelength on the determination of the quantity of CO to detect the presence of water droplet blockage. In the plot shown in FIG. 5, water droplets were present in optical path 130. This can be seen from the manner in which the quantity of HC moves inversely proportionally with the determined residual impact of water droplet blockage at the first absorption wavelength on the determination of the quantity of CO.

If, on the other hand, water droplet blockage were not present, the residual impact of water droplet blockage at the first absorption wavelength on the determination of the quantity of CO were not proportional (e.g., inversely proportional) to the determined quantity of HC, water analysis module 218 may determine that water droplets were not present in optical path 130.

Figure 6:
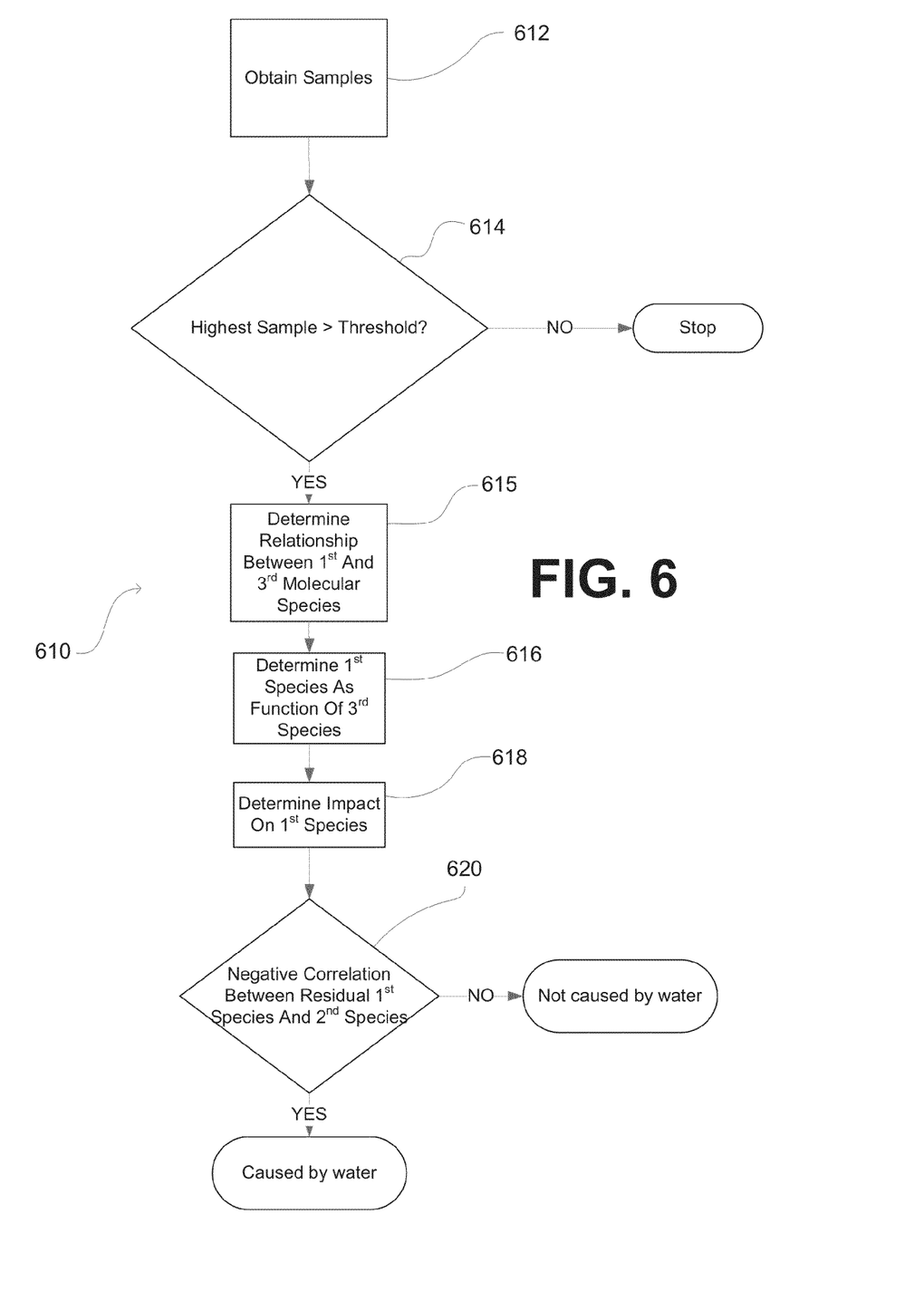
FIG. 6 is an exemplary illustration of a flowchart of processing operations for detecting the presence of water droplets in the optical path of an RSS system, according to an aspect of the invention.

FIG. 6 is an exemplary illustration of a flowchart of processing operations for detecting the presence of water droplets in the optical path of an RSS system, according to an aspect of the invention. The processing operations of method 610 presented below are intended to be illustrative. In some implementations, method 610 may be accomplished with one or more additional operations not described, and/or without one or more of the operations discussed. Additionally, the order in which the operations of method 610 are illustrated in FIG. 6 and described below is not intended to be limiting.

In some implementations, method 610 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 610 in response to instructions stored electronically on an electronic storage medium. The one or more processing devices may include one or more devices configured through hardware, firmware, and/or software to execute one or more of the operations of method 610.

In an operation 612, series of samples related to quantities of molecular species present in an exhaust plume may be obtained. The series of samples may have been obtained by RSS 110 (as described above and illustrated in FIGS. 1 and 2). The series of samples may include, for example, a series of samples related to the quantity of CO, a series of samples related to the quantity of HC, and/or a series of samples related to the quantity of $CO_2$. The series of samples may include a series of samples of absorption in a first absorption wavelength associated with CO, a series of samples of absorption in a second absorption wavelength associated with HC, and/or a series of samples of absorption in a third wavelength associated with $CO_2$. The series of samples may include a series of samples of measured quantity of CO, a series of samples of measured quantity of HC, and/or a series of samples of measured quantity of $CO_2$.

In an operation 614, a series of samples associated with CO may be may be analyzed to determine if an analysis for detecting the presence of water droplets in the exhaust plume should be performed. Determining if the analysis should be performed may include comparing samples related to the quantity of HC with a threshold. In some implementations, operation 614 may be performed by a trigger module that is the same as or similar to trigger module 214 (shown in FIG. 2 and described above). If it is determined in operation 614 that the analysis should be performed, method 610 may proceed to an operation 615.

In operation 615, a relationship between the quantity of CO and $CO_2$ may be determined. This relationship may describe the quantity of the first molecular species as a function of the quantity of $CO_2$. Operation 615 may include, for example, determining a regression line that plots samples related to the quantity of CO against contemporaneously measured samples of related to the quantity of $CO_2$. In some implementations, operation 614 may be performed by a residual module that is the same as or similar to residual module 216 (as shown in FIG. 2 and described above).

In an operation 616, the quantity of CO may be determined as a function of the quantity of $CO_2$. This determination may be made using the relationship determined in operation 615. In some implementations, operation 616 may be performed by a residual module that is the same as or similar to residual module 216 (as shown in FIG. 2 and described above).

In an operation 618, the quantity of CO determined according to the function determined at operation 616 may be removed from the samples related to the quantity of CO obtained in operation 612. If water droplet blockage is present in the samples related to the quantity of CO obtained at operation 612, operation 618 may result in the determination of the residual impact of water droplet blockage on the determination of the quantity of CO. In some implementations, operation 618 may be performed by a residual module that is the same as or similar to residual module 216 (as shown in FIG. 2 and described above).

In an operation 620, the values obtained in operation 618 are analyzed in conjunction with the samples related to the quantity of HC obtained in operation 612 to determine whether water droplets were present in the exhaust plume. In some implementations, operation 620 may be performed by a water analysis module that is the same as or similar to water analysis module 218 (as shown in FIG. 2 and described above).

If it is determined in operation 620 that water droplets were present in the exhaust plume one or more of the samples related to the quantity of HC may be discarded as being inaccurate, may be corrected to adjust for the impact of the water, and/or may otherwise be processed.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any implementation can be combined with one or more features of any other embodiment.

What is claimed is:

1. A system for detecting the presence of water droplets in vehicle emissions, the system comprising:
   one or more processors configured to execute computer program modules, the computer program modules comprising:
   (i) a quantity module configured to obtain measurements of quantities of carbon monoxide, hydrocarbons, and carbon dioxide present in an exhaust plume emitted by a vehicle based on information related to intensities of electromagnetic in a plurality of absorption wavelengths, the plurality of absorption wavelengths comprising a first absorption wavelength that corresponds to carbon monoxide, a second absorption wavelength that corresponds to hydrocarbons, and a third absorption wavelength that corresponds to carbon dioxide;
   (ii) a residual module configured to determine an impact on determinations of the quantity of carbon monoxide caused by blockage of electromagnetic radiation at the first absorption wavelength by water droplets by:
      determining the quantity of carbon monoxide as a function of the measured quantity of carbon dioxide; and
      subtracting the quantity of carbon monoxide determined as a function of the measured carbon dioxide from the obtained measurement of the quantity of carbon monoxide; and
   (iii) a water analysis module configured to detect the presence of water droplets based on a comparative analysis of the measured quantities of hydrocarbons and the determined impact on determinations of the quantity of carbon monoxide caused by blockage of electromagnetic radiation at the first absorption wavelength by water droplets.

2. The system of claim 1, wherein the residual module is further configured to determine a relationship that describes the quantity of carbon monoxide as a function of the measured quantity of carbon dioxide.

3. The system of claim 1, wherein the water analysis module is configured to detect the presence of water droplets if the determined impact on determinations of the quantity of carbon monoxide caused by blockage of electromagnetic radiation at the first absorption wavelength is inversely proportional to the measured quantities of hydrocarbons.

4. A method of detecting the presence of water droplets in vehicle emissions, the method comprising:
   obtaining measurements of quantities of carbon monoxide, hydrocarbons, and carbon dioxide present in an exhaust plume emitted by a vehicle based on information related to intensities of electromagnetic radiation in a plurality of absorption wavelengths, the plurality of absorption wavelengths comprising a first absorption wavelength that corresponds to carbon monoxide, a second absorption wavelength that corresponds to hydrocarbons, and a third absorption wavelength that corresponds to carbon dioxide;
   (ii) determining, via one or more processors, an impact on determinations of the quantity of carbon monoxide caused by blockage of electromagnetic radiation at the first absorption wavelength by water droplets by:
      determining the quantity of carbon monoxide as a function of the measured quantity of carbon dioxide; and
      subtracting the quantity of carbon monoxide determined as a function of the measured quantity of carbon dioxide from the obtained measurement of the quantity of carbon monoxide; and
   (iii) detecting the presence of water droplets based on a comparative analysis of the measured quantities of hydrocarbons and the determined impact on determinations of the quantity of carbon monoxide caused by blockage of electromagnetic radiation at the first absorption wavelength by water droplets.

5. The method of claim 4, wherein determining an impact on determinations of the quantity of carbon monoxide caused by blockage of electromagnetic radiation at the first absorption wavelength by water droplets further comprises determining a relationship that describes the quantity of carbon monoxide as a function of the measured quantity of carbon dioxide.

6. The method of claim 5, wherein determining the relationship that describes the quantity of carbon monoxide as a function of the measured quantity of carbon dioxide comprises determining a regression line that correlates the obtained measurements of carbon monoxide with the obtained measurements of carbon dioxide.

7. The method of claim 4, wherein the presence of water droplets is detected responsive to the determined impact on determinations of the quantity of carbon monoxide caused by blockage of electromagnetic radiation at the first absorption wavelength being inversely proportional to the obtained quantities of the first molecular species.

* * * * *